United States Patent [19]
Arruego et al.

[11] Patent Number: 6,152,901
[45] Date of Patent: Nov. 28, 2000

[54] BLOOD SAMPLING DEVICE WITH VACUUM TUBE

[75] Inventors: Daniel P. Arruego, Chicheboville; Alain B. Lloze, Amaye sur Orne, both of France

[73] Assignee: Altair, Argences, France

[21] Appl. No.: 09/347,358

[22] Filed: Jul. 6, 1999

[30] Foreign Application Priority Data

Jul. 3, 1998 [FR] France ................................. 98 08551

[51] Int. Cl.$^7$ .................................................. A61M 5/00
[52] U.S. Cl. ........................... 604/195; 128/763; 604/263
[58] Field of Search ................................. 604/195, 187, 604/110, 198, 263; 128/763–765

[56] References Cited

U.S. PATENT DOCUMENTS

| 4,846,808 | 7/1989 | Haber et al. ........................ 128/763 X |
| 5,070,885 | 12/1991 | Bonaldo ................................ 128/763 |
| 5,125,414 | 6/1992 | Dysarz ................................... 128/763 |
| 5,337,756 | 8/1994 | Barbier et al. ........................ 128/763 |
| 5,423,758 | 6/1995 | Shaw ..................................... 604/110 |
| 5,487,734 | 1/1996 | Thorne et al. ........................ 604/195 |
| 5,800,395 | 9/1998 | Botich et al. ........................ 604/195 X |

FOREIGN PATENT DOCUMENTS

WO/89/04141  5/1989  WIPO .

*Primary Examiner*—John B. Yasko
*Attorney, Agent, or Firm*—Finnegan, Henderson, Farabow, Garrett & Dunner, L.L.P.

[57] ABSTRACT

A blood sampling device for introducing a blood sample into a vacuum tube including a pierceable stopper, the device comprising: a tubular body including a side wall provided with at least one longitudinal slot ending in rear and front enlargements, and a front transverse wall provided with an orifice and a cannula having a front part and a rear part extending on either side of a side housed in the tubular body and cooperating with the longitudinal slot, the slide being displaceable between a rear end position in which it is located in the rear enlargement of the slot while the front and rear parts of the cannula are situated inside the tubular body, and a front end position in which it is locked in the front enlargement of the slot while the front part of the cannula passes through the orifice in the transverse wall of the tubular body and protrudes from the latter for the purpose of implanting it in a sampling zone and introducing a blood sample into the vacuum tube, after the latter has been placed in the tubular body and the stopper has been pierced by the rear end of the cannula. A safety device is provided for immobilizing the slide definitively in its rear end position when the latter has been brought back into this position after being locked in the front enlargement of the longitudinal slot to prevent reuse of the sampling device.

10 Claims, 4 Drawing Sheets

BLOOD SAMPLING DEVICE WITH VACUUM TUBE

The present invention relates to a blood sampling device for introducing a blood sample into a vacuum tube including a pierceable stopper, said device comprising:

a tubular body including a side wall provided with at least one longitudinal slot ending in rear and front enlargements, and a front transverse wall provided with an orifice; and a cannula having a front part and a rear part extending on either side of a slide housed in the tubular body and cooperating with the longitudinal slot, the slide being displaceable between a rear end position in which it is locked in the rear enlargement of the slot while the front and rear parts of the cannula are situated inside the tubular body, and a front end position in which it is locked in the front enlargement of the slot while the front part of the cannula passes through the orifice in the transverse wall of the tubular body and protrudes from the latter for the purpose of implanting it in a sampling zone and introducing a blood sample into the vacuum tube, after the latter has been placed in the tubular body and the stopper has been pierced by the rear end of the cannula.

The current blood sampling devices can be used several times, which can have serious consequences for the health of the persons subjected to the sampling procedures.

The present invention proposes preventing such reuse and, to do so, its subject is a blood sampling device which comprises safety means for immobilizing the slide definitively in its rear end position when the latter has been brought back into this position after being locked in the front enlargement of the longitudinal slot.

By virtue of these safety means, the sampling device according to the invention can no longer be re-used after it has been once used. The risks of contamination of the persons subjected to the sampling procedures are thus eliminated in full.

Furthermore, as the cannula is entirely inside the tubular body when the slide is in its rear end position, the persons manipulating the sampling devices are protected against accidental stick injuries and consequently against the risks of contamination.

According to a particular embodiment of the invention, the safety means comprise movable members situated on the slide and fixed members situated on the inner face of the front transverse wall of the tubular body.

According to this embodiment, the movable members can comprise:

an elastic arch including at least one stud displaceable between a retracted position in which it is entirely inside the tubular body, and an advanced position in which it is at least partially outside the tubular body and projects into a lateral notch formed in the rear enlargement of the longitudinal slot, and a hook displaceable between an active position in which it engages with the arch and holds the stud in its retracted position, and an inactive position in which it is separated from the arch and allows the stud to come into its advanced position when the slide is brought back into its rear end position.

As regards the fixed members, they comprise a finger intended to displace the hook from its active position to its inactive position when the slide comes into its front end position.

Thus, when the slide reaches its front end position, the finger carried by the transverse wall of the tubular body automatically displaces the hook from its active position to its inactive position. The arch, which is elastic, then springs outward once the hook frees it. Then, when the slide is brought back into its rear end position, the stud reaches its advanced position inside the lateral notch of the rear enlargement of the longitudinal slot and immobilizes the slide definitively.

The slide can advantageously comprise a control member carried by a second elastic arch situated behind the arch bearing the stud, the control member being stressed radially outward by the second arch and including a pusher projecting outside the longitudinal slot, a shoulder whose extent corresponds to that of the enlargements of the longitudinal slot, and a guide zone which is situated between the pusher and the shoulder and whose width corresponds to that of the part of the longitudinal slot which is situated between the front and rear enlargements.

Being stressed radially outward by the second arch, the control member locks the slide when the latter is in its initial rear end position or in its front end position.

This is because the shoulder of the control member is situated each time in one of the enlargements of the longitudinal slot and prevents a longitudinal displacement of the slide along the latter.

To be able to effect such a displacement, it is first necessary to exert pressure on the pusher in order to bring the guide zone in front of the longitudinal slot, and then to exert on the pusher a longitudinal thrust in the desired direction.

The shoulder can preferably include two transverse tabs turned toward one another and forming between them a seat into which the second arch is snap-fitted.

During manufacture of the sampling device according to the invention, the slide, without the control member, is introduced into the tubular body, said introduction being of course carried out from the open end of the tubular body.

It is in fact only after placing the slide in its rear end position that the shoulder of the control member is snap-fitted onto the second arch.

Such an operation is easy to perform, especially when the material from which the slide is made has a certain elasticity. It suffices to exert pressure on the control member so that the transverse tabs of the shoulder move apart and allow the second arch to lodge itself in the seat formed between them.

According to an important characteristic of the invention, the pusher has a grip surface whose extent is determined such that it covers the rear enlargement of the longitudinal slot of the tubular body as well as the lateral notch of this enlargement, when the slide is in its rear end position.

The extent of the grip surface is chosen so that it covers the stud when the slide is in its rear end position and prohibits fraudulent unlocking of the latter with the aid of a tool or the like.

The slide can preferably comprise a third arch which is situated in front of the arch bearing the stud and whose external dimensions correspond, except for the sliding clearance, to the internal dimensions of the tubular body.

By virtue of this third arch, the slide can be guided in a very reliable manner, which prevents its becoming jammed and avoids any risk of malfunction of the sampling device.

According to a first alternative embodiment, the cannula is bent at an angle, its front and rear parts being parallel to one another, the first being adjacent to the side wall of the tubular body while the second is coaxial or practically coaxial with the latter.

As the front part of the cannula is adjacent to the side wall of the tubular body, it can be implanted in the sampling zone by placing the sampling device in a position practically level with the sampling zone, which makes the practitioner's task easier.

Furthermore, as the rear part of the cannula is coaxial or practically coaxial with the axis of the tubular body, it reliably pierces the stopper of the vacuum tube being used.

According to a second alternative embodiment, the cannula is rectilinear and extends parallel to the tubular body, between the axis and the periphery thereof.

This second alternative has the advantage of being less costly to produce, while at the same time allowing the sampling device to be placed in a more level position than in the case of the current devices and nevertheless allowing the stopper of the vacuum tube to be pierced with certainty.

According to another characteristic of the invention, the tubular body includes, at its open rear end, an external flange whose periphery is shaped so as to constitute a nonstable support surface.

It is therefore impossible to place the sampling device vertically on a table or any other support surface. The risks of a person suffering a stick injury in the case of the slide not having been brought back into its rear end position are thus very greatly reduced.

Three embodiments of the present invention will be described below by way of nonlimiting examples, with reference to the attached drawings in which.

Figure 9:
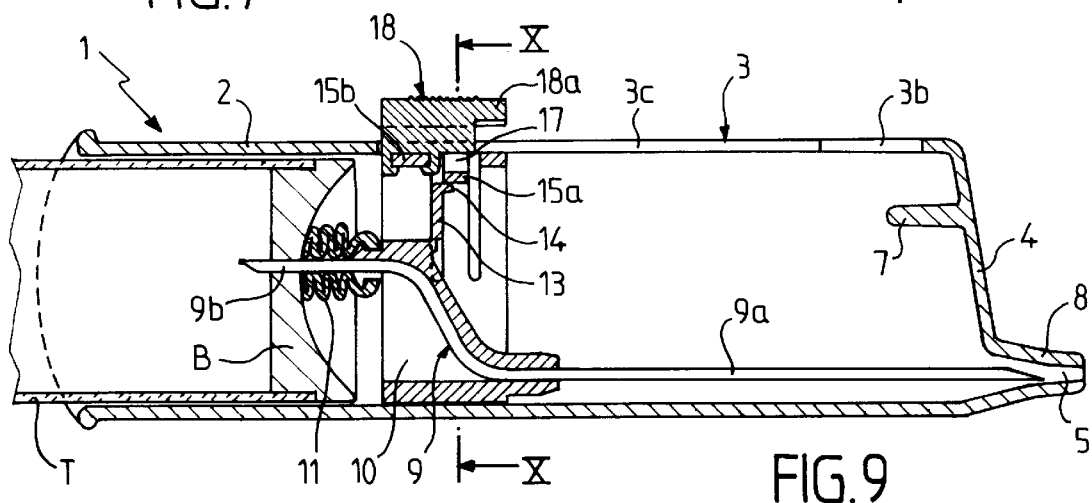
FIG. 9 is a longitudinal sectional view of the sampling device, the slide having been brought back into its rear end position.

The blood sampling devices shown in the drawings are intended for introducing a blood sample into transparent tubes, such as tube T shown partially in FIG. 9.

These tubes, in which a vacuum is maintained by means of pierceable stoppers B, for example made of rubber, are of conventional design and obviously do not form part of the invention.

The sampling device shown in FIGS. 1 to 10 comprises a tubular body 1 including a side wall 2 provided with a longitudinal slot 3, and a front transverse wall 4 provided with an orifice 5.

The tubular body 1 is preferably made of a transparent plastic material. Its side wall 2 has a triangular shape in cross section, while its open rear end includes an external flange 6 shaped so as to prevent its standing when placed directly on a support such as a table or laboratory bench top.

Figure 3:
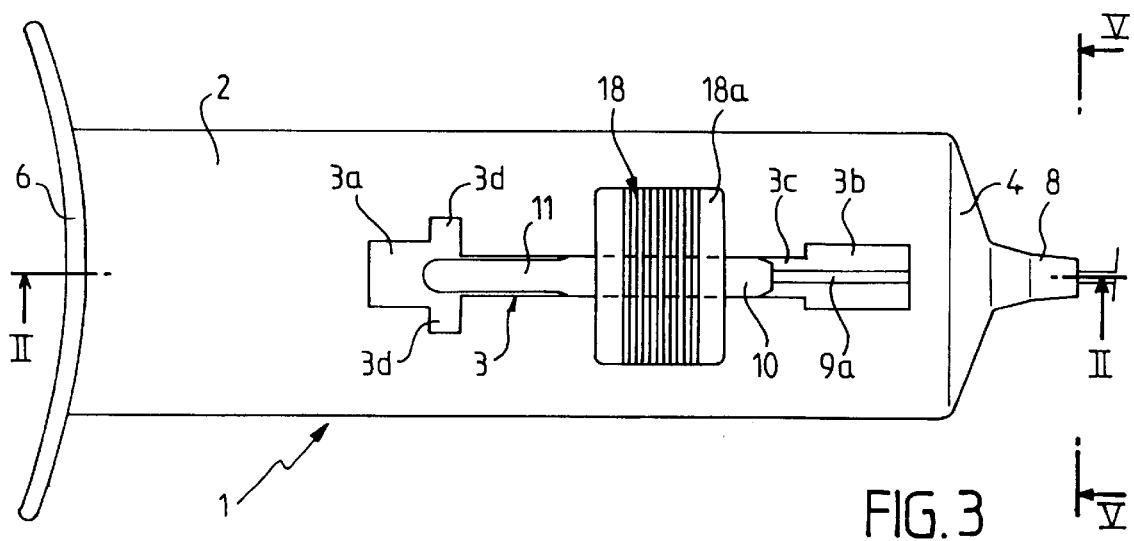
FIG. 3 is a plan view of the device shown in FIG. 2.
Figure 4:
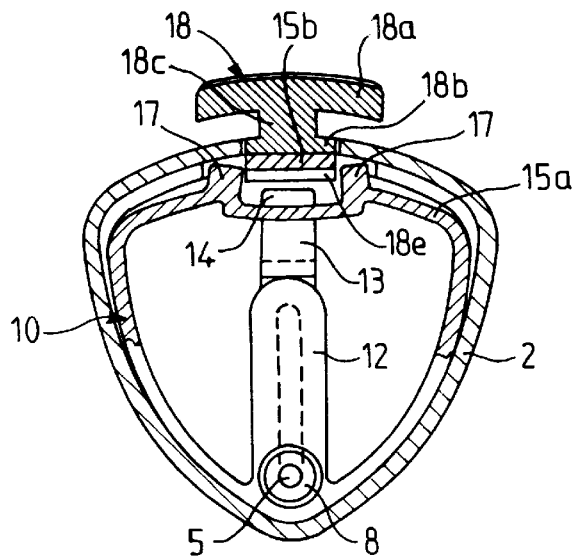
FIG. 4 is a sectional view on the line IV—IV in FIG. 1.
Figure 5:
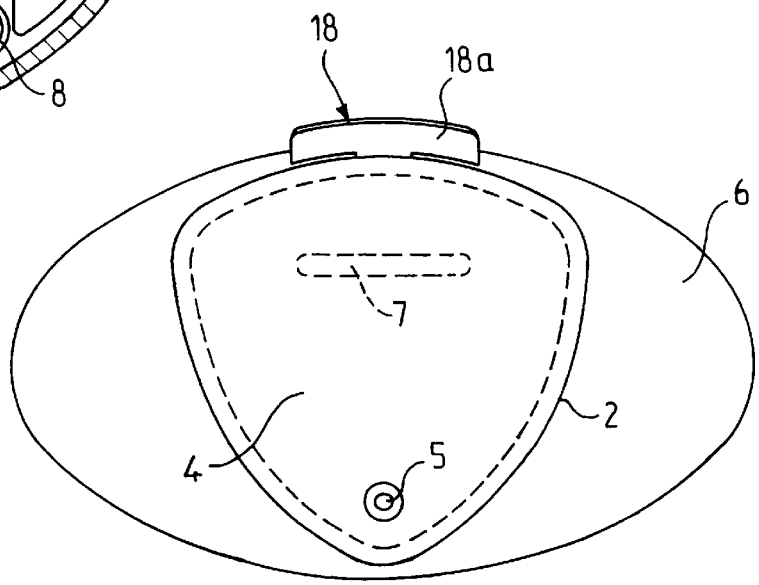
FIG. 5 is a view on the line V—V in FIG. 3.

As FIGS. 3 and 5 show, the flange 6 has an elliptic shape and a constant thickness and forms a concave dish surrounding the open end of the tubular body 1. By virtue of its elliptic shape, the flange 6 prevents the sampling device from rolling along a support and falling off.

The longitudinal slot 3 includes a rear end enlargement 3a and a front end enlargement 3b which are connected via an intermediate part 3c of constant width.

The rear enlargement 3a has the shape of a T, of which the transverse branch is made up of two rectangular notches 3d situated toward the front enlargement 3b.

As regards the front enlargement 3b, this is rectangular and has a width equal to that of the longitudinal branch of the T constituting the rear enlargement 3a.

Furthermore, the front transverse wall 4 of the tubular body 1 is provided on its inner face with a finger 7, whose role will be explained below, and on its outer face with a tubular projection 8 whose internal conduit constitutes the orifice 5.

It will be noted here that the axis of the orifice 5 is parallel to the longitudinal axis of the tubular body 1.

The sampling device also comprises a cannula 9 extending on either side of a slide 10 housed in the tubular body 1 and cooperating with the longitudinal slot 3.

The cannula 9 includes a front part 9a intended to be inserted into a vein for the purpose of taking a blood sample, and a rear part 9b intended to pierce the stopper B of a vacuum tube T designed to receive the blood sample taken.

This cannula is bent at an angle and its front 9a and rear 9b parts are parallel to one another, the first being adjacent to the side wall 2 of the tubular body 1, while the second is coaxial with the latter.

Referring to the drawings, it will be observed that the rear part 9b of the cannula is covered by a protective cap 11 made of rubber.

The slide 10 is displaceable in the tubular body 1 between a rear end position (which can be seen in FIGS. 1 and 4) in which it is locked in the rear enlargement 3a, 3d of the slot 3, and a front end position (which can be seen in FIG. 7) in which it is locked in the front enlargement 3b of the slot 3.

When the slide 10 is in its rear end position, the front 9a and rear 9b parts of the cannula 9 are both situated inside the tubular body. By contrast, when it is in its front end position, the front part 9a of the cannula projects from the tubular body 1 in the area of the orifice 5 and can thus be inserted into a vein.

It is of course necessary to introduce a tube T into the tubular body 1 so that the rear part 9b of the cannula pierces the stopper B and so that the partial vacuum in the tube ensures introduction into the latter of a sample of blood coming from the vein in which the front part 9a of the cannula has been implanted.

Figure 6:
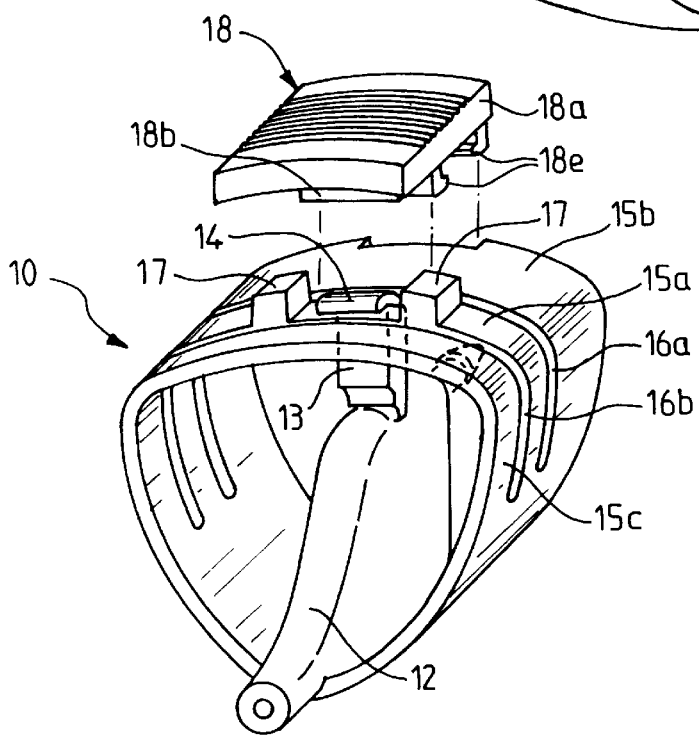
FIG. 6 is a perspective view of the slide, the pusher being detached from its arch.
Figure 7:
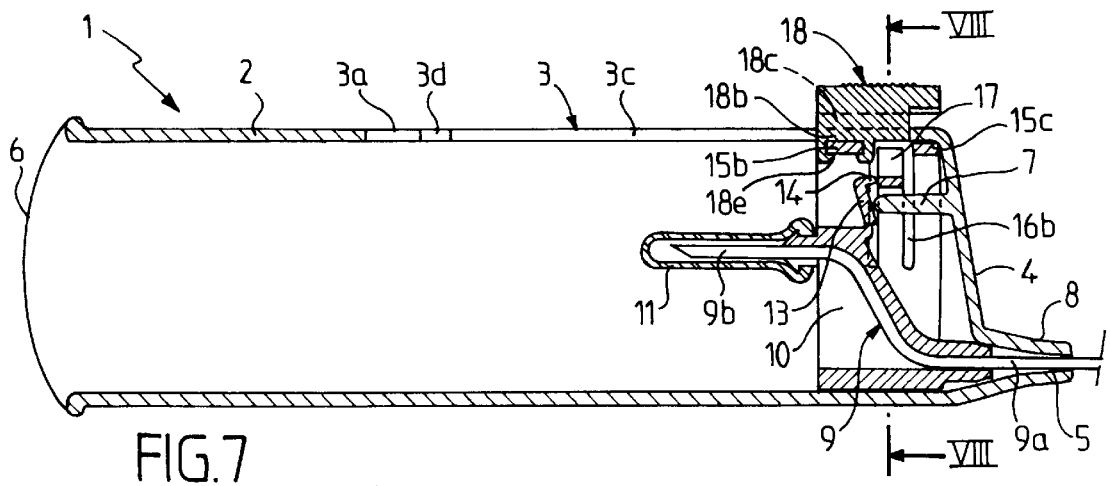
FIG. 7 is a longitudinal sectional view of the sampling device, the slide being in its front end position.

The slide 10 comprises a tubular body whose cross section is practically the same as that of the tubular body 1 and which is particularly clear in FIG. 6.

A protuberance 12 extending axially inside the slide occupies a little more than the lower half of the latter. It surrounds the angled part of the cannula 9 and renders the latter integral with the slide. In addition, it is provided with a hook 13 whose role will be described below, this hook projecting upward from the highest part of the protuberance and ending in a tongue 14 turned toward the front transverse wall 4 of the tubular body 1.

Approximately the upper half of the side wall of the slide 10 is divided into three arches 15a, 15b and 15c by two transverse slots 16a, 16b.

The arch 15a, designated as the first arch or intermediate arch, bears, on its outer face, two studs 17 whose extent and distance correspond to those of the rectangular notches 3d of the rear enlargement 3a of the slot 3.

Figure 1:
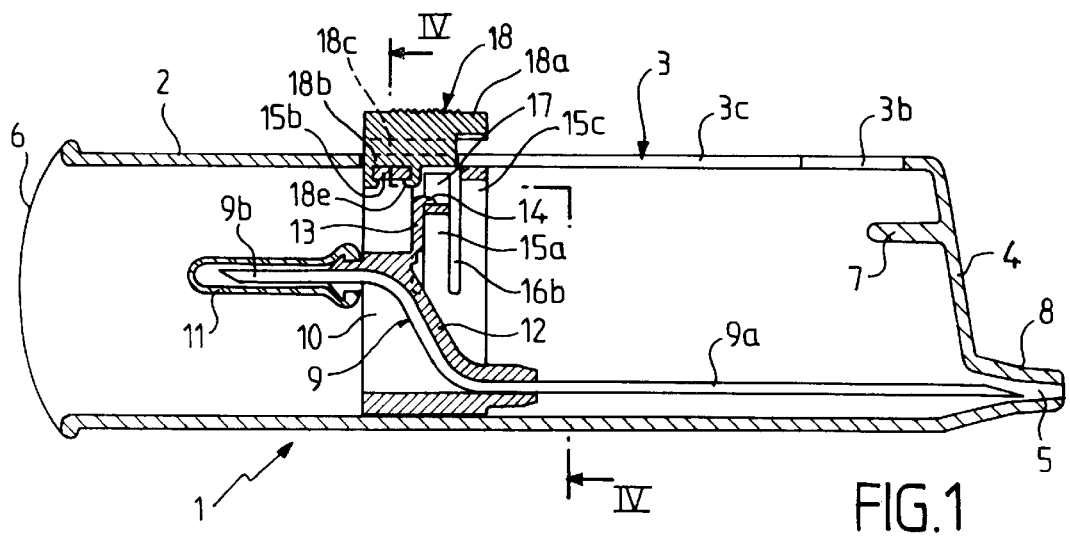
FIG. 1 is a longitudinal sectional view of a first sampling device according to the invention, the slide being in its initial rear end position.

The hook 13 mentioned above is in engagement with the arch 15a and prevents the studs 17 from penetrating into the notches 3d when the slide is in its initial front end position shown in FIG. 1.

The arch 15b, designated as the second arch or rear arch, is situated on the side away from the front transverse wall 4 of the tubular body 1 and supports a control member 18 with the aid of which a user can move the slide 10 along the slot 3.

The control member 18 includes a pusher 18a projecting from the slot 3, a shoulder 18b whose extent corresponds to that of the front 3b and rear 3a enlargements (except for the notches 3d) of the slot, and a guide zone 18c which is situated between the pusher 18a and the shoulder 18b and whose width corresponds to that of the intermediate part 3c of the slot 3.

The pusher 18a has a rectangular grip surface which, when the slide 10 is in its rear end position, entirely covers the rear enlargement 3 and its notches 3d and thereby prevents any access to the studs 17.

Furthermore, the shoulder 18b includes, on its lower face, two transverse tabs 18e turned toward one another and forming between them a seat in which the rear arch 15b is snap-fitted.

The arch 15c, designated as the third arch or front arch, is provided to facilitate the displacement of the slide 10 inside the tubular body 1. For this purpose, its external dimensions correspond, except for the sliding clearance, to the internal dimensions of the tubular body 1.

The operations which have to be performed in order to use the sampling device according to the invention will now be described.

It should first be pointed out that this device is delivered with the slide 10 in its rear end position, as shown in FIG. 1.

In this position, the hook 13 is in engagement with the intermediate arch 15a and prevents the studs 17 from projecting into the notches 3d of the rear enlargement 3a of the longitudinal slot of the tubular body 1.

By contrast, the shoulder 18b projects into the rear enlargement 3a and counters any longitudinal movement of the slide 10 in the direction of the front wall 4 of the tubular body.

In order to move the slide toward this wall, it is in fact necessary to exert pressure on the pusher 18a in order to bring the guide zone 18c to the level of the longitudinal slot 3, and then to push the pusher 18a in the direction of the transverse wall 4.

During this time, the front part 9a of the cannula advances into the orifice 5 and gradually projects outward from the tubular body.

Figure 2:
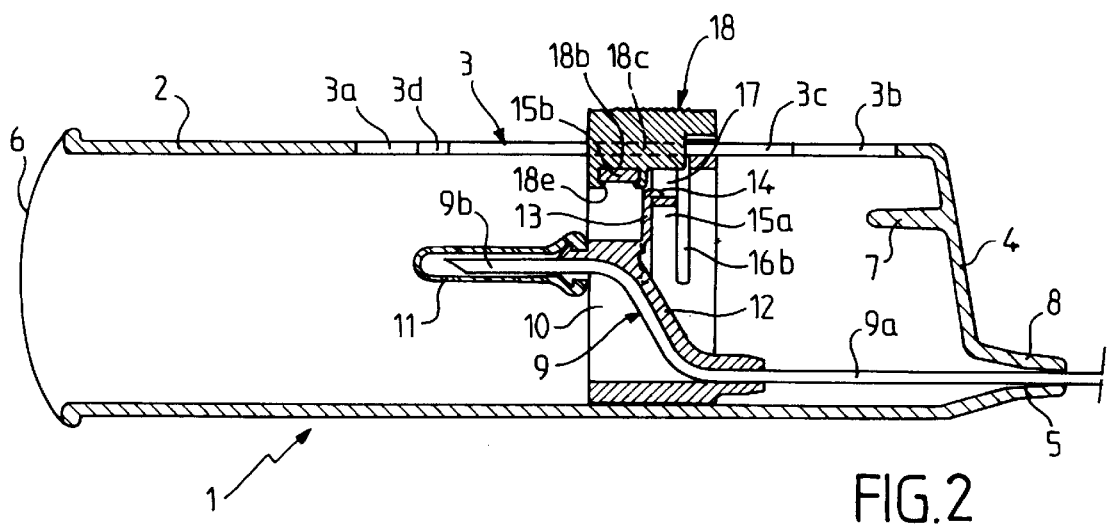
FIG. 2 is a sectional view on the line II—II in FIG. 3, the slide being between its rear and front end positions.

Referring to FIG. 2, it will be observed that the studs 17 and the shoulder 18b are inside the tubular body and that the hook 13 is still in engagement with the arch 15a.

Then, when the slide 10 reaches its front end position, the shoulder 18b projects elastically into the front enlargement 3b of the longitudinal slot 3, while the finger 7 provided on the inner face of the transverse wall 4 pushes the hook 13 rearward and detaches it from the arch 15a.

Figure 8:
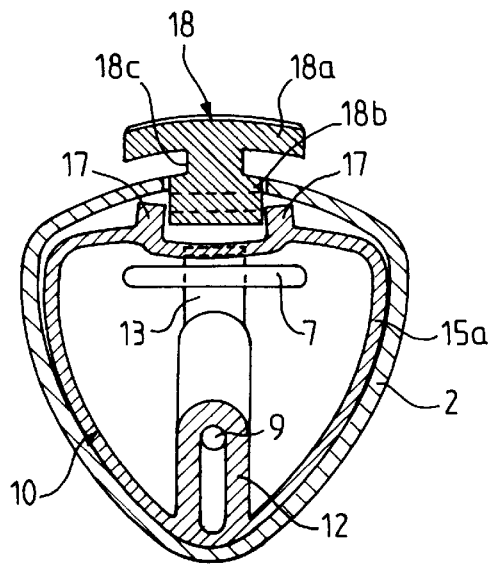
FIG. 8 is a sectional view on the line VIII—VIII in FIG. 7.

By reason of the elasticity of the material used to make the slide 10, the studs 17 come to bear against the inner surface of the longitudinal wall 2 of the tubular body 1, as shown in FIG. 8.

As the shoulder 18b is situated in the front enlargement 3b, the slide 10 is locked in such a way that the sampling device can be used to introduce a blood sample into a tube T.

After the sample has been taken, it is necessary to exert pressure once again on the pusher 18a in order to bring the guide zone 18c to the level of the longitudinal slot 3, and then to push the pusher 18a in such a way as to distance it from the transverse wall 4.

Then, when the slide reaches its rear end position, the shoulder 18b projects elastically into the rear enlargement 3a.

Figure 10:
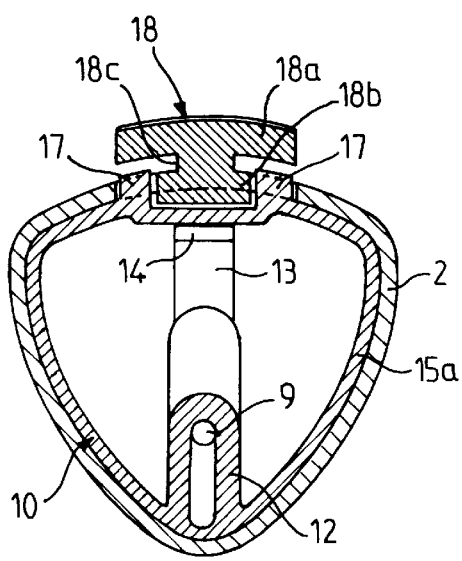
FIG. 10 is a sectional view on the line X—X in FIG. 9.

Simultaneously, the studs 17 move elastically into the notches 3d of the enlargement 3a, as shown in FIG. 10, while the tongue 14 of the hook 13 comes elastically under the arch 15a and counters any lowering of the latter, as shown in FIG. 9.

It is now impossible to bring the slide 10 back into its front end position and to carry out another sampling procedure.

This is because exerting pressure on the pusher 18a does not permit extraction of the studs 17 from the notches 3d. Furthermore, as the pusher entirely covers the notches 3d, it is impossible to access the studs with the aid of a tool or the like and thus to extract them fraudulently from said notches.

It will be evident from what has been stated above that the sampling device according to the invention is designed to be used only once, which eliminates the risks of contamination of patients.

Furthermore, as the cannula 9 is contained entirely within the tubular body 1 when the slide 10 has been brought back into its rear end position, the risks of the person carrying out the blood sampling procedure being accidentally injured are eliminated.

Figure 11:
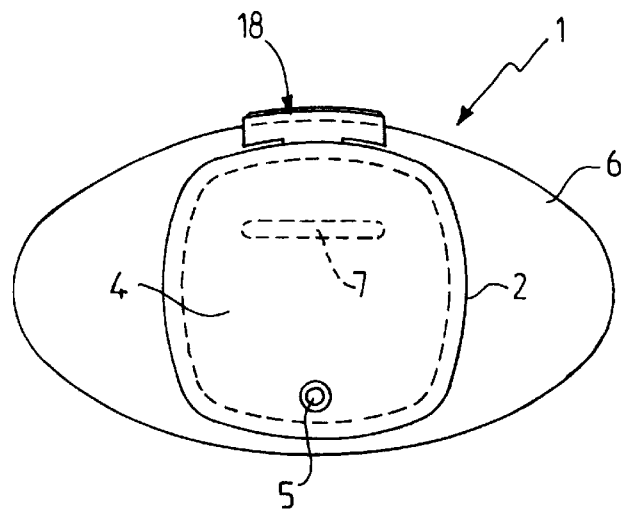
FIG. 11 is an end view of a second sampling device according to the invention, this view being taken from the direction of the front part of the cannula.

Referring now to FIG. 11, it will be observed that the sampling device shown in this figure has a tubular body 1 with a practically square cross section and rounded corners.

It goes without saying that it would not be departing from the scope of the present invention if the tubular body had a circular cross section.

Figure 12:
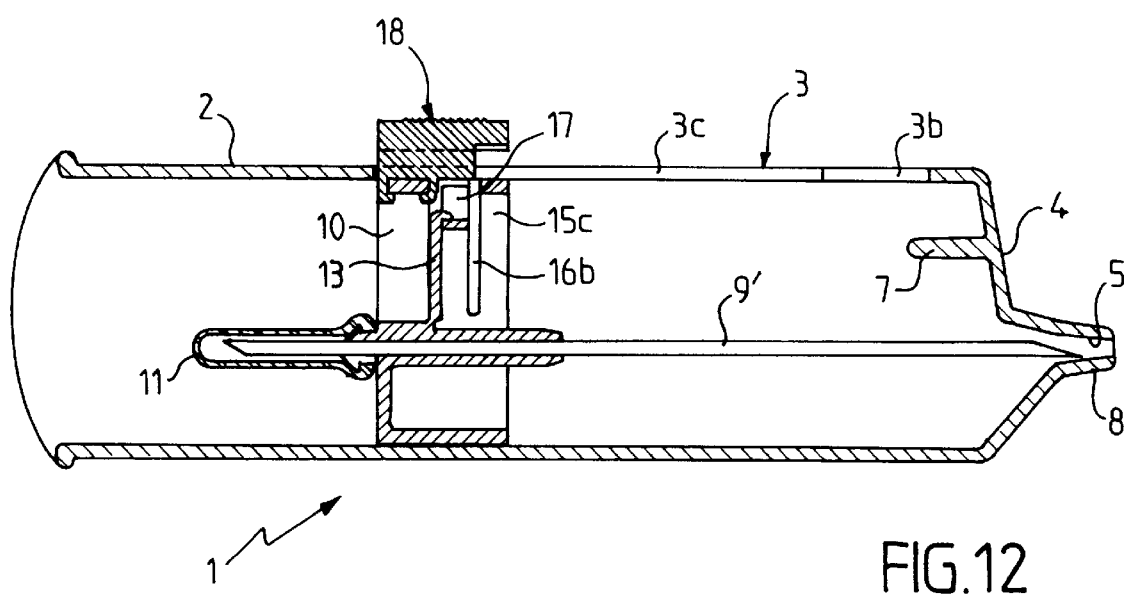
FIG. 12 is a longitudinal sectional view of a third sampling device according to the invention.

Finally, referring to FIG. 12, it will be observed that the sampling device shown includes a rectilinear cannula 9' extending parallel to the tubular body 1, this cannula being situated in an intermediate position between the longitudinal axis of the tubular body and the longitudinal wall thereof.

What is claimed is:

1. A blood sampling device for introducing a blood sample into a vacuum tube (T) including a pierceable stopper (B), said device comprising:

a tubular body (1) including a side wall (2) provided with at least one longitudinal slot (3) ending in rear (3a) and front (3b) enlargements, and a front transverse wall (4) provided with an orifice (5);

a cannula (9; 9') having a front part (9a) and a rear part (9b);

a slide (10) carrying the cannula (9; 9') and cooperating with the longitudinal slot (3), the slide being displaceable in the tubular body (1) between a rear end position in which the front (9a) and rear (9b) parts of the cannula (9; 9') are situated inside the tubular body (1), and a front end position in which the front part (9a) of the cannula (9; 9') passes through the orifice (5) in the transverse wall (4) of the tubular body (1) and protrudes from the latter for the purpose of taking a blood sample and introducing the latter into the vacuum tube (T); and safety means (7, 13, 14, 15a, 17) for immobilizing the slide (10) definitively in its rear end position when it has been brought back into this position after the sample has been taken, the safety means comprising movable members (13, 14, 15a, 17) situated on the slide (10) and fixed members (7) situated on the tubular body (1), wherein the movable members comprise:

an elastic arch (15a) including at least one stud (17) displaceable between a retracted position in which it is entirely inside the tubular body (1), and an advanced position in which it is at least partially outside the tubular body (1) and projects into a lateral notch (3d) formed in the rear enlargement (3a) of the longitudinal slot (3), and a hook (13, 14) displaceable between an active position in which it engages with the arch (15a) and holds the stud (17) in its retracted position, and an inactive position in which it is separated from the arch (15a) and allows the stud (17) to come into its advanced position when the slide (10) is brought back into its rear end position.

2. The device as claimed in claim 1, wherein the fixed members are situated on the inner face of the front transverse wall (4) of the tubular body (1).

3. The device as claimed in claim 2, wherein the fixed members comprise a finger (7) intended to displace the hook (13, 14) from its active position to its inactive position when the slide (10) comes into its front end position.

4. The device of claim 3, wherein the slide (10) comprises a control member (18) carried by a second elastic arch (15b) situated behind the arch (15a) bearing the stud (17), the control member being stressed radially outward by the second arch (15b) and including a pusher (18a) projecting outside the longitudinal slot (3), a shoulder (18b) whose extent corresponds to that of the enlargements (3a, 3b) of the longitudinal slot (3), and a guide zone (18c) which is situated between the pusher (18a) and the shoulder (18b) and whose width corresponds to that of the part of the longitudinal slot (3) which is situated between the front (3b) and rear (3a) enlargements.

5. The device as claimed in claim 4, wherein the shoulder (18b) includes two transverse tabs (18e) turned toward one another and forming between them a seat into which the second arch (15b) is snap-fitted.

6. The device as claimed in claim 5, wherein the pusher (18a) has a grip surface whose extent is determined such that it covers the rear enlargement (3a) of the longitudinal slot (3) of the tubular body (1) as well as the lateral notch (3d) of this enlargement, when the slide (10) is in its rear end position.

7. The device of claim 6, wherein the slide (10) comprises a third arch (15c) which is situated in front of the arch (15a) bearing the stud (17) and whose external dimensions correspond, except for the sliding clearance, to the internal dimensions of the tubular body (1).

8. The device of claim 7, wherein the cannula (9) is bent at an angle, its front (9a) and rear (9b) parts being parallel to one another, the first being adjacent to the side wall (2) of the tubular body (1) while the second is coaxial or practically coaxial with the latter.

9. The device of claim 7, wherein the cannula (9') is rectilinear and extends parallel to the tubular body (1), between the axis and the periphery thereof.

10. The device of claim 1, wherein the tubular body (1) includes, at its open rear end, an external flange (6) whose periphery is shaped so as to constitute a nonstable support surface.

* * * * *